United States Patent [19]

Eguchi et al.

[11] Patent Number: 4,666,707

[45] Date of Patent: May 19, 1987

[54] WEAKLY ACIDIC BATH SALT COMPOSITION

[75] Inventors: Yasuteru Eguchi; Hidenori Yorozu, both of Utsunomiya, Japan

[73] Assignee: Kao Corporation, Tokyo, Japan

[21] Appl. No.: 718,459

[22] Filed: Apr. 1, 1985

[30] Foreign Application Priority Data

Apr. 12, 1984 [JP] Japan .................................. 59-73509

[51] Int. Cl.$^4$ ................................................ A61L 9/04
[52] U.S. Cl. ...................................................... 424/44
[58] Field of Search ........................................... 424/44

[56] References Cited

PUBLICATIONS

Wells et al. "Cosmetics and the Skin" 1964, pp. 323–333.

Balsam et al. "Cosmetics, Science and Technology", vol. 2, 2nd ed; 1972, pp. 504–505 & 516–519.

Primary Examiner—Leonard Schenkman
Attorney, Agent, or Firm—Oblon, Fisher, Spivak, McClelland & Maier

[57] ABSTRACT

Into a weakly acidic bath additive composition comprising a carbonate salt and an acid, a moisturizer is further incorporated. Typical examples of the moisturizer include organic acid salts such as sodium lactate; polyhydric alcohols such as propylene glycol; water-soluble polymers such as polyethylene glycol; and so on.

The moisturizer functions to keep the carbon dioxide gas to stay in the bath, thereby enhances the blood circulation promoting effect of the carbon dioxide gas.

9 Claims, No Drawings

WEAKLY ACIDIC BATH SALT COMPOSITION

BACKGROUND OF THE INVENTION (i) Field of the Invention:

This invention relates to a novel, weakly acidic bath salt composition and, more particularly, to a weakly acidic bath salt composition which comprises a carbonate salt and an acid for providing the bath with a weakly acidic pH and further a moisturizer for synergistically increasing the blood circulation promoting effect and feeling of moistness of the skin.

(ii) Description of the Prior Art:

Generally, bath salt compositions are prepared by incorporating perfume, colorant, plant extract, organic acid and so on into an inorganic salt mixture comprising sodium sulfate, borax, sulfur, sodium chloride, carbonate salt, etc., and are used for the purpose of providing the bath with perfume and/or color, or adequately stimulating the skin to thereby promote the blood circulation, the recovery from fatigue and/or the metabolism. Among such bath salt compositions, there are foaming bath salt compositions comprising a combination of a carbonate salt and an acid, which produce, in the bath, carbon dioxide gas bubbles to thereby cause a relaxing or refreshing sensation and render bathing enjoyable.

However, the prior art foaming bath salt compositions are neutral or weakly alkaline, so that the carbon dioxide gas generated is little dissolved in water but escapes into the air. Thus, the carbon dioxide gas bubbles can produce only a mechanical, sensational effect.

SUMMARY OF THE INVENTION

Accordingly, the present inventors conducted an extensive and intensive study and developed a weakly acidic bath salt composition containing a carbonate salt and an acid and giving the bath a weakly acidic pH and thus causing retention of the carbon dioxide gas in the bath to thereby promote blood circulation and prevent the chill after bathing. Furthermore, the present inventors have now found that the incorporation of a moisturizer into said bath salt composition leads to synergistic increase in the blood circulating promoting effect and moist feeling to the skin, and have completed the present invention.

Thus, the invention provides a weakly acidic bath salt composition comprising a carbonate salt and an acid with a moisturizer further incorporated therein.

DETAILED DESCRIPTION OF THE INVENTION AND PREFERRED EMBODIMENTS

The carbonate salt to be incorporated in the weakly acidic bath salt composition according to the invention includes, among others, sodium hydrogen carbonate, sodium carbonate, sodium sesquicarbonate, potassium hydrogen carbonate, potassium carbonate, potassium sesquicarbonate, ammonium hydrogen carbonate, ammonium carbonate and ammonium sesquicarbonate. These may be used either alone or in combination of two or more.

The acid to be used may be either an organic acid or an inorganic acid, and preferably is a water-soluble solid one. The organic acid includes, among others, formic acid, straight-chain aliphatic acids such as acetic acid, propionic acid, butyric acid and valeric acid; dicarboxylic acids such as oxalic acid, malonic acid, succinic acid, glutaric acid, adipic acid, pimelic acid, fumaric acid, maleic acid, phthalic acid, isophthalic acid and terephthalic acid; acidic amino acids such as glutamic acid and aspartic acid; hydroxy acids such as glycolic acid, lactic acid, hydroxyacrylic acid, $\alpha$-hydroxybutyric acid, glyceric acid, tartronic acid, malic acid, tartaric acid, hydroxybenzoic acid, citric acid, salicylic acid (o, m, p), gallic acid, mandelic acid, tropic acid, ascorbic acid and gluconic acid; cinnamic acid, benzoic acid, phenylacetic acid, nicotinic acid, kainic acid, sorbic acid, pyrrolidonecarboxylic acid, trimellitic acid, benzenesulfonic acid and toluenesulfonic acid; and acidic salts of these organic acids. The inorganic acids includes, among others, phosphoric acid, potassium dihydrogen phosphate, sodium dihydrogen phosphate, sodium sulfite, potassium sulfite, sodium pyrosulfite (sodium metabisulfite), potassium pyrosulfite (potassium metabisulfite), acidic sodium hexametaphosphate, acidic potassium hexametaphosphate, acidic sodium pyrophosphate, acidic potassium pyrophosphate and sulfamic acid. Among others preferred are aliphatic dicarboxylic acids such as succinic acid, and fumaric acid and phosphoric acid as well as acidic salts of these.

Typical examples of the moisturizer to be used in the present invention are as follows:
(1) Organic acid salts such as sodium lactate, disodium tartrate, sodium pyrrolidonecarboxylate and disodium glutamate;
(2) Polyhydric alcohols such as propylene glycol, 1,3-butylene glycol, glycerol and sorbitol;
(3) Water-soluble macromolecules such as polyethylene glycol, polyvinyl alcohol, sodium alginate and polyvinylpyrrolidone;
(4) Mucopolysaccharides such as chondroitin sulfate and hyaluronic acid;
(5) Collagen and derivatives thereof; and
(6) Nucleic acids (DNA, RNA), proteins such as elastin, keratin, fibroin, and hydrolyzates thereof.

The ratio between the carbonate salt and the acid in the bath salt composition according to the invention is required to be such that when added to the bath, the bath salt composition renders the bath weakly acidic, namely such that a 0.01 weight percent aqueous solution of the bath salt composition has a pH of 4 to 7, preferably 6.0 to 6.7. When the pH is lower than 4, the stimulation to the skin becomes severe and at the same time there is the risk of damaging the bath heater and the like. At a pH exceeding 7, the effect of the invention cannot be produced.

The effect of the invention is based on the principle that, on the acidic side of pH, carbon dioxide occurs as the $CO_2$ molecule and produces the blood circulation promoting effect whereas, on the alkaline side of pH, carbon dioxide occurs as the $CO_3^{2-}$ or $HCO_3^-$ ion, so that said effect cannot be produced at all.

The proportion of carbonate salt to acid to satisfy such condition may vary depending on the kind of carbonate salt and of acid but, preferably, the carbonate salt accounts for 5 to 80% by weight (hereinafter referred to as % for brevity), more preferably 10 to 50%, and the acid accounts for 10 to 80%, more preferably 15 to 50%, based on the whole composition.

The moisturizer may be incorporated in an amount varying in a wide range. Generally, however, it is used in an amount of 0.001 to 10%, preferably 0.01 to 2%, on the whole composition basis.

The bath salt composition according to the invention may further contain ingredients generally used in this sort of composition, such as fragrance material, coloring matter, vitamins, effective ingredients of spring, protease, lanoline, silicone, crude drug or extract thereof, etc., so that the desired effect can be further increased.

The weakly acidic bath salt composition according to the invention may take the form of powder, granules, crystals, tablets and so forth, preferably tablets. In preparing such forms, an excipient, binder, disintegrating agent, lubricant, and so forth may be added as necessary.

As mentioned above, the weakly acidic bath salt composition according to the invention has a pH almost equal to the pH of the human skin and accordingly can exert favorable influence on the skin. While carbon dioxide produced upon throwing a bath slat composition into the bath occurs as an ion when the resulting bath is alkaline, failing to exhibit the blood circulation promoting effect, carbon dioxide can occur as a $CO_2$ molecule in the acidic region as attained according to the invention and shows a marked blood circulation promoting effect.

The following examples illustrate the invention in further detail.

EXAMPLE 1

Bath salt compositions were prepared according to the formulations given in Table 1. Each bath salt composition was evaluated for global impression thereof as a bath salt composition (overall evaluation), occurrence or non-occurrence of chill after bathing, and moistness of the skin by 30 panelists who used the composition for 1 month in the conventional manner by throwing it into the bath to make a 0.01% aqueous solution.

The results obtained are shown in Table 2.

TABLE 1

| Ingredient (%) | Composition According to the Invention | | | Composition for Comparison |
|---|---|---|---|---|
| | 1 | 2 | 3 | 4 |
| Anhydrous sodium sulfate | 29 | 29 | 29 | 30 |
| Sodium hydrogen carbonate | 55 | 55 | 55 | 65 |
| Succinic acid | 15 | 15 | 15 | 5 |
| Sodium alginate | 0.2 | | | |
| Sodium pyrrolidone-carboxylate | | 0.5 | | |
| Collagen hydrolyzate (MW = 1,000) | | | 0.3 | |
| Colorant | suitable amount | suitable amount | suitable amount | suitable amount |
| Fragrance | suitable amount | suitable amount | suitable amount | suitable amount |
| Form | Tablets | Tablets | Tablets | Tablets |
| pH of 0.01% aqueous solution | 6.1 | 6.1 | 6.1 | 7.5 |

TABLE 2

| Comparison | Evaluation | Composition of the invention is better | Equivocal | Composition for comparison is better |
|---|---|---|---|---|
| Composition 1 and Composition 4 for comparison | Global evaluation | 25 | 1 | 4 |
| | Chill after bath | 27 | 0 | 3 |
| | Skin moistness | 28 | 2 | 0 |
| Composition 2 and Composition 4 for comparison | Global evaluation | 26 | 1 | 3 |
| | Chill after bath | 20 | 5 | 5 |
| | Skin moistness | 29 | 1 | 0 |
| Composition 3 and Composition 4 for comparison | Global evaluation | 30 | 0 | 0 |
| | Chill after bath | 28 | 2 | 0 |
| | Skin moistness | 27 | 1 | 2 |

What is claimed is:

1. A weakly acidic bath salt composition, comprising:
   (1) 5 to 80% by weight of a carbonate salt,
   (2) 10 to 80% by weight of an acid, and
   (3) 0.001 to 10% by weight of a moisturizer.

2. The weakly acidic bath sale composition of claim 1, wherein the said carbonate salt is at least one member selected from the group consisting of sodium hydrogen carbonate, sodium carbonate, sodium sesquicarbonate, potassium hydrogen carbonate, potassium carbonate, potassium sesquicarbonate, ammonium hydrogen carbonate, ammonium carbonate and ammonium sesquicarbonate.

3. The weakly acidic bath salt composition of claim 1, wherein the said acid is at least one member selected from the group consisting of formic acid, acetic acid, propionic acid, butyric acid, valeric acid, oxalic acid, malonic acid, succinic acid, glutaric acid, adipic acid, pimelic acid, fumaric acid, maleic acid, phthalic acid, isopthalic acid, terephthalic acid, glutamic acid, aspartic acid, α-hydroxybutyric acid, glyceric acid, tartronic acid, malic acid, tartaric acid, hydroxybenzoic acid, citric acid, salicyclic acid (o, m, p), gallic acid, mandelic acid, tropic acid, ascorbic acid, gluconic acid, cinnamic acid, benzoic acid, phenylacetic acid, nicotinic acid, kainic acid, sorbic acid, pyrrolidonecarboxylic acid, trimellitic acid, benzenesulfonic acid, toluenesulfonic acid, phosphoric acid, potassium dihydrogen phosphate, sodium dihydrogen phosphate, sodium sulfite, potassium sulfite, sodium pyrosulfite, potassium pyrosulfite, acidic sodium hexametaphosphate, acidic potassium hexametaphosphate, acidic sodium pyrophoshate, acid potassium pyrophosphate, sulfamic acid, glycolic acid, lactic acid, and hydroxyacrylic acid.

4. The weakly acidic bath salt composition of claim 3, wherein the said acid is succinic acid, fumaric acid, phosphoric acid, acidic sodium hexametaphosphate, acidic potassium hexametaphosphate, acid sodium pyrophosphate or acidic potassium pyrophosphate.

5. The weakly acidic bath salt composition of claim 1, wherein the said moisturizer is at least one member selected from the group consisting of sodium lactate, disodium tartrate, sodium pyrrolidonecarboxylate, disodium glutamate, propylene glycol, 1,3-butylene glycol, glycerol, sorbitol, polyethylene glycol, polyvinyl alcohol, sodium alginate, polyvinylpyrrolidone, chondroitin sulfate, hyaluronic acid, Collagen and derivatives thereof, Nucleic acids (DNA, RNA), elastin, keratin, fibroin, keratin hydrolyzates and fibroin hydrolyzates.

6. The weakly acidic bath salt composition of claim 7, wherein a 0.01 weight percent aqueous solution of the said bath salt composition has a pH of 6.0 to 6.7.

7. The weakly acidic bath salt composition of claim 1, wherein a 0.01 weight percent aqueous solution of the said bath salt composition has a pH of 4 to 7.

8. The weakly acidic bath salt composition of claim 1, wherein the moisturizer is present in an amount of 0.01 to 2% by weight of the composition.

9. A weakly acidic bath salt composition, comprising:
(1) 5 to 80% by wt. of a carbonate salt which is at least one member selected from the group consisting of sodium hydrogen carbonate, sodium carbonate, sodium sesquicarbonate potassium hydrogen carbonate, potassium carbonate, potassium sesquicarbonate, ammonium hydrogen carbonate, ammonium carbonate, and ammonium sesquicarbonate;
(2) 10 to 80% by wt. of an acid which is at least one member selected from the group consisting of formic acid, acetic acid, propionic acid, butyric acid, valeric acid, oxalic acid, malonic acid, succinic acid, glutaric acid, adipic acid, pimelic acid, fumaric acid, maleic acid, phthalic acid, isophthalic acid, terephthalic acid, glutamic acid, aspartic acid, ahydroxybutyric acid, glyceric acid, tartronic acid, malic acid, tartaric acid, hydrobenzoic acid, citric acid, salicyclic acid (o, m, p), gallic acid, mandelic acid, tropic acid, ascorbic acid, gluconic acid, cinnamic acid, benzoic acid, phenylacetic acid, niootinic acid, kainic acid, sorbic acid, pyrrolidonecarboxylic acid, trimellitic acid, benzenesulfonic acid, toluenesulfonic acid, phosphoric acid, potassium dihydrogen phosphate, sodium dihydrogen phosphate, sodium sulfite, potassium sulfite, sodium pyrosulfite, potassium pyrosulfite, acidic sodium hexametaphosphate, acidic potassium hexametaphosphate, acidic sodium pyrophosphate, acidic potassium pyrophosphate, sulfamic acid, glycolic acid, lactic acid, and hydroxyacrylic acid; and
(3) 0.001 to 10% by wt. of a moisturizer which is at least one member selected from the group consisting of sodium lactate, disodium tartrate, sodium pyrrolidonecarboxylate, disodium glutamate, propylene glycol, 1,3-butylene glycol, glycerol, sorbitol, polyethylene glycol, polyvinyl alcohol, sodium alginate, polyvinylpyrrolidone, chondroitin sulfate, hyaluronic acid, collagen and derivatives thereof, nucleic acids (DNA, RNA), elastin, keratin, fibroin, keratin hydrolyzates and fibroin hydrolyzates.

* * * * *